United States Patent
Hernandez (10) Patent No.: US 11,865,138 B2
(45) Date of Patent: Jan. 9, 2024

(54) METHODS AND COMPOSITIONS FOR THERAPEUTIC SKIN TREATMENTS IN DERMATOLOGICAL PROCEDURES AFFECTING SKIN'S BARRIER

(71) Applicant: Topix Pharmaceuticals, Inc., North Amityville, NY (US)

(72) Inventor: Steven M. Hernandez, Blue Point, NY (US)

(73) Assignee: Topix Pharmaceuticals, Inc., North Amityville, NY (US)

(*) Notice: Subject to any disclaimer, the term of this patent is extended or adjusted under 35 U.S.C. 154(b) by 0 days.

(21) Appl. No.: 17/497,436

(22) Filed: Oct. 8, 2021

(65) Prior Publication Data

US 2022/0110967 A1  Apr. 14, 2022

Related U.S. Application Data

(60) Provisional application No. 63/089,903, filed on Oct. 9, 2020.

(51) Int. Cl.

| | |
|---|---|
| *A61K 31/728* | (2006.01) |
| *A61K 31/375* | (2006.01) |
| *A61K 31/19* | (2006.01) |
| *A61K 9/00* | (2006.01) |
| *A61K 45/06* | (2006.01) |
| *A61P 17/02* | (2006.01) |
| *A61P 1/02* | (2006.01) |

(52) U.S. Cl.
CPC .......... *A61K 31/728* (2013.01); *A61K 9/0014* (2013.01); *A61K 9/0021* (2013.01); *A61K 31/19* (2013.01); *A61K 31/375* (2013.01); *A61K 45/06* (2013.01); *A61P 1/02* (2018.01)

(58) Field of Classification Search
CPC .. A61K 31/728; A61K 9/0014; A61K 9/0021; A61K 31/19; A61K 31/375; A61K 45/06; A61P 17/02

USPC .......................................................... 514/54
See application file for complete search history.

(56) References Cited

U.S. PATENT DOCUMENTS

| | | |
|---|---|---|
| 2006/0134095 A1 | 6/2006 | Ito et al. |
| 2011/0158922 A1* | 6/2011 | Dupont ................... A61P 17/10 |
| | | 424/59 |
| 2019/0000740 A1 | 1/2019 | Wiebensjo et al. |
| 2019/0151214 A1 | 5/2019 | Shaffer et al. |
| 2019/0216871 A1* | 7/2019 | Rehm ..................... A61K 8/42 |
| 2020/0268618 A1 | 8/2020 | Hernandez |

FOREIGN PATENT DOCUMENTS

| | | |
|---|---|---|
| CN | 105878051 A | 8/2016 |
| CN | 105878051 * | 2/2019 |
| WO | 2022010683 A1 | 1/2022 |

OTHER PUBLICATIONS

Glossary of medical education terms, Institute of International Medical Education. http://www.iime.org/glossary.htm Accessed in Mar. 2013. (Year: 2013).*
Huang et al. The Truth About Over-the-Counter Topical Anti-Aging Products: A Comprehensive Review. Aesthetic Surg J 2007; 27: 402-412. (Year: 2007).*
Hyaluronic Acid | Skin Care Raw Materials | Centerchem. https://www.centerchem.com/products/hyaluronic-acid [accessed on Apr. 8, 2023] (Year: 2023).*
Interntional Search Report and Written Opinion for PCT/US2021/054194 dated Feb. 24, 2022, 9 pages.

* cited by examiner

*Primary Examiner* — Yih-Horng Shiao
(74) *Attorney, Agent, or Firm* — Lowenstein Sandler LLP (57) ABSTRACT

Disclosed in certain embodiments are skincare formulations and treatment methods having hyaluronic acid, or its associated salts, and one or more of ascorbic acid, glycolic acid or lactic acid. In certain embodiments, the formulations and treatments are applied to the skin during and/or before and/or after dermatological procedures that affect the skin's barrier for alleviating patient discomfort and enabling rapid healing of irritated and damaged skin.

16 Claims, 2 Drawing Sheets

METHODS AND COMPOSITIONS FOR THERAPEUTIC SKIN TREATMENTS IN DERMATOLOGICAL PROCEDURES AFFECTING SKIN'S BARRIER

CROSS REFERENCE TO RELATED APPLICATIONS

The present application claims priority to U.S. provisional application No. 63/089,903 filed on Oct. 9, 2020, the entire contents of which are incorporated in its entirety by reference.

TECHNICAL FIELD

The present invention relates to the field of therapeutic treatments and compositions for skincare, including skincare treatments and formulations for application to the skin. For example, some skincare treatments may include dermatological procedures that affect the skin's barrier to reduce scarring and post-inflammatory hyper-pigmentation, and patient discomfort and to enable rapid healing of the skin. Methods for application to the skin, formulation, manufacture and use thereof are also presented.

BACKGROUND

Various dermatological procedures, such as microneedling, laser, chemical peels, intense light therapy, microdermabrasion or derma-planing, are used to treat and improve conditions such as acne scarring, fine lines and wrinkles, loose skin, skin texture, pore size, brown spots, stretch marks, and pigment issues. Such procedures tend to disrupt the skin's barrier or cause redness, irritation, inflammation, among other skin conditions, which need to be addressed and corrected.

In microneedling procedures, the skin is prepared to facilitate microneedling. In some cases, the depth of the needles may draw blood, which may irritate and/or inflame the skin. Other anti-aging and corrective skin procedures may involve chemical, thermal and mechanical wounds. Patients undergoing such treatments have extremely irritated and sensitive skin after the treatment requiring further treatment post-procedure. Some treatments may include applying, for example, cold compresses, wet soaks or occlusive ointments. However, some post-treatments may cause further irritation and inflammation, rather than alleviate the post-procedure condition being treated, and often the post-treatments may be ineffective.

When the skin is prepared for a dermatological procedure, such as microneedling, that disrupts the skin's barrier, a skin treatment may be used. The constituent ingredients of the skin treatment are limited because certain active agents cannot be used when the skin is inflamed and irritated by the procedures. In particular, dermatological procedures that disrupt, i.e., wound, the skin's barrier tend to make the skin sensitive to most skin treatments, such that the skin treatment may not be used. Thus, stronger active agents are not used during or immediately before and/or after these dermatological procedures. Instead, wet pads having water and/or other soothing liquids are applied to relieve patient discomfort.

Accordingly, there is a need in the art for improved formulations that can be used with dermatological procedures that affect the skin's barrier to reduce patient discomfort, scarring and post-inflammatory hyper-pigmentation, stimulate collagen growth, and provide effective healing to the skin of those undergoing treatments of the type noted above. More specifically, there is a need in the art for improved skincare formulations and methods that are used, during and/or before and/or after procedures, such as microneedling, to provide effective healing and repair of the skin's barrier.

SUMMARY OF THE PRESENT INVENTION

The present disclosure provides formulations for skincare and method of skincare treatment thereof. More particularly, disclosed in certain embodiments are therapeutic treatments and formulations having a therapeutically effective amount of hyaluronic acid, or salts thereof, such as sodium hyaluronate, and optionally one or more alpha hydroxy acid (AHA). In certain embodiments of the present disclosure, the skincare treatment and formulation may optionally include one or more organic acids, such as ascorbic acid, glycolic acid, or lactic acid.

In some embodiments of the present disclosure, formulation may comprise hyaluronic acid and/or sodium hyaluronate, water, one or more AHA or combinations thereof, one or more antioxidant or combinations thereof, or one or more peptide or combinations of peptides.

In some embodiments, the formulation may include sodium hyaluronate in an amount of at least 0.00001% w/w, at least 0.0001% w/w, at least 0.001% w/w, at least 0.01% w/w, at least 0.01% w/w, at least 0.05% w/w or at least 0.1% w/w. In other embodiments, the formulation may include sodium hyaluronate in an amount of at most 0.001% w/w, at most 0.01% w/w, at most 0.1% w/w, at most 1% w/w, at most 2% w/w, at most 5% w/w or at most 10% w/w. In certain embodiments, the sodium hyaluronate is in a range with any of the lower limits or higher limits disclosed above. In other embodiments, the formulation may include one or more of ascorbic acid, glycolic acid, or lactic acid, wherein each is at least 0.001 ppm, at least 0.01 ppm, or at least 1 ppm, at least 5 ppm or at least 10 ppm. In other embodiments, the formulation may include one or more of ascorbic acid, glycolic acid, or lactic acid, wherein each is at most 1 ppm, at most 10 ppm, or most 50 ppm, at most 80 ppm or at most 100 ppm The disclosed embodiments may treat, e.g., melasma, i.e., hyper-pigmentation, including post-inflammatory hyper-pigmentation, patient discomfort, scarring, stimulate collagen growth, and provide effective healing to the skin of those undergoing treatments of the type noted above.

Certain active agents, such as ascorbic acid, glycolic acid, or lactic acid, are not to be used during and/or immediately before and/or after dermatological procedures, such as microneedling, due to their strong effect on the disrupted, i.e., wounded, irritated skin barrier. However, such active agents by virtue of certain embodiments of the present invention are beneficial in various ways, including, but not limited to, treating melasma, i.e., hyper-pigmentation, including post-inflammatory hyper-pigmentation, patient discomfort, scarring, stimulating collagen growth, and providing effective healing to the skin of those undergoing treatments of the type noted above.

The present inventors surprisingly have found that when such active agents are used, e.g., in amounts disclosed herein, for example, 1 ppm, and combined with a salt of hyaluronic acid, e.g., a solution of honeycomb array sodium hyaluronate, the formulation with other optional active agents, as also disclosed hereinafter, may be used in dermatological procedures. In particular, the present inventors surprisingly have found that certain embodiments of the formulation disclosed herein are effectively used during and/or before and/or after microneedling procedures, that disrupt the skin's barrier, so as to provide unexpected and surprising results for the patients' skin.

For example, the formulation of the present disclosure may be applied to a patient's skin to undergo dermatological procedures before the procedure, rubbed into the skin, for example, with a gloved hand, the skin then wiped to remove excess solution, if any. The dermatological procedure is then performed after a short while, e.g., immediately, within 1 minute, within 5 minutes, within 10 minutes, within 30 minutes, within 1 hours or within 2 hours so that the applied formulation penetrates the skin's barrier. In procedures such as microneedling, laser, and intense light therapy, the penetrative effects of the procedures drive or push the applied formulation into the skin barrier because the procedure disrupts the skin's barrier. For example, in microneedling, the needles "tattoo" the applied formulation into the skin. The formulation can the be performed after the procedure (optionally after cleaning), e.g., immediately, within 10 minutes, within 30 minutes, within 1 hour, within 4 hours, or within 6 hours. It can then be optionally applied thereafter, e.g., once daily, twice daily, three timed daily or four times daily.

Surprisingly and unexpectedly, the formulation includes active agents that previously could not be used during these procedures due to intense discomfort to the patients; the present inventors have found that the formulation disclosed herein is effectively used to provide beneficial results for the patients' skin. Once the dermatological procedure has been completed, the formulation may be reapplied and left on the patients' skin to continue to provide therapeutic and other beneficial affects to the patients. Previously it was not possible to use formulations having, for example, active agents, such as ascorbic acid, glycolic acid, lactic acid, on patients' skin with disrupted, i.e., severely irritated, skin barrier. Unexpectedly, the present inventors have noted surprising results when the formulation disclosed herein is used in dermatological procedures, including, but not limited to, the treatment of melasma, i.e., hyper-pigmentation, including post-inflammatory hyper-pigmentation, patient discomfort, scarring, the stimulation of collagen growth, and providing effective healing to the skin of those undergoing treatments of the type noted above.

In certain embodiments, the compositions exhibit low irritancy, and improved, synergistic efficiency of the formulated ingredients, including improved alleviation of discomfort and healing in the subjects. In particular, the present disclosure provides in certain embodiments therapeutic treatments with a formulation having a combination of components, which exhibit lower irritancy, better regression time, and improved penetration properties of all the formulated active ingredients into the skin as compared with other skincare products.

In some embodiments, the formulation of the present disclosure may be used as pre-treatment and/or post-treatment agents for skincare treatments, such as microneedling. As discussed in further detail below, the formulation of certain embodiments of the present disclosure has enhanced discomfort relief and provide enhanced healing of the skin in conditions arising from dermatological procedures that disrupt the skin's barrier.

In some embodiments, the present disclosure provides a formulation including sodium hyaluronate, such as hydrolyzed sodium hyaluronate. In some embodiments of the present disclosure, other combinations of active ingredients disclosed herein may achieve the desired improved treatment results. Surprisingly, it has been found that the combination of hyaluronic acid, or salts thereof, such as sodium hyaluronate, and an organic acid, such as ascorbic acid, glycolic acid, and/or lactic acid, yields surprising and unexpected results for healing and irritation relief in skincare procedures.

In some embodiments, the formulation may also comprise one or more moisturizer and/or humectant. In one aspect of this embodiment, the moisturizer and/or humectant is sodium hyaluronate, such as fractionated and long-chain sodium hyaluronate, from single monomer to about 5 million Daltons, to bind moisture to the skin and penetrate the skin carrying moisture.

In some embodiments, the formulation may also comprise skin soothing agents, such as antioxidants, to reduce skin inflammation and irritation.

In some embodiments, the treatment may also comprise one or more soothing antioxidants to calm the skin and reduce inflammation. In one embodiment, the antioxidant is a polyphenol. In another embodiment, the antioxidant includes a polyphenol isolate of *Camellia sinensis*.

In certain embodiments of the present disclosure, a method for therapeutic treatment of skin in dermatological procedures affecting the skin's barrier is provided. The method may include applying a therapeutically effective amount of a formulation to skin selected for a dermatological procedure affecting the skin's barrier, wherein the formulation includes hyaluronic acid, or salts thereof, and one or more of ascorbic acid, glycolic acid, of lactic acid, wherein the hyaluronic acid or its associated salts is at least 1% (w/w) and each of the ascorbic acid, glycolic acid, lactic acid is at least 1 ppm; and performing the dermatological procedure on the skin.

In some embodiments, the dermatological procedure may include microneedling, laser, chemical peels, intense light therapy, microdermabrasion, and/or derma-planing. In certain embodiments, performing the dermatological procedure includes applying a microneedling procedure to the skin, wherein the formulation may be applied before the microneedling procedure and/or after the microneedling procedure.

In some embodiments, after a procedure of the present invention the skin may have a reduction in scarring of at least about any of 5%, 10%, 15%, 20%, 25%, 40%, 50%, 60%, 75% or 90%, e.g., as compared to a procedure without application of the formulations disclosed herein. In other embodiments, after a procedure of the present invention the skin may have a reduction in scar depth of from any of about 5%, about 10%, about 20%, about 25% or about 40% to any of about 30%, about 50%, about 60%, about 80% or about 99%, e.g., as compared to a procedure without application of the formulations disclosed herein In some embodiments, the salt of hyaluronic acid may be sodium hyaluronate. In other embodiments, the sodium hyaluronate may be a solution of honeycomb array sodium hyaluronate. In further embodiments of the present disclosure, the formulation may further include an antioxidant, wherein the antioxidant is one or more of *Camellia sinensis* leaf extract, *Camellia sinensis* polyphenols, ascorbic acid, ubiquinone, bisabolol, Thiotaine® ergothioneine, glutathione, or superoxide dismutase. In some embodiments, the formulation may further include one or more of purified water, hydrolyzed sodium hyaluronate, sodium hyaluronate, *Camellia sinensis* leaf extract, benzyl alcohol, ubiquinone, bisabolol, Thiotaine®, TEGO PEP 417®, Matrixyl® (glycerin, butylene glycol, carbomer, polysorbate 20, palmitoyl pentapeptide-4), glutathione, superoxide dismutase, phenoxyethanol, sodium benzoate, or disodium EDTA. In certain embodiments of the present disclosure, the formulation may be a sterile formulation.

In some embodiments of the present disclosure, a formulation may provide for therapeutic treatment of skin in dermatological procedures affecting the skin's barrier. The formulation may include hyaluronic acid, or salts thereof, and one or more of ascorbic acid, glycolic acid, lactic acid, wherein the hyaluronic acid or salts thereof is at least 1% (w/w) and each of the ascorbic acid, glycolic acid, or lactic acid is at least 1 ppm.

In certain embodiments of the present disclosure, the formulation may comprise (% w/w): purified water (50%-99.8%); hydrolyzed sodium hyaluronate (0%-25%); sodium hyaluronate (0.1%-10%); *Camellia sinensis* leaf extract (0%-1%); ascorbic acid (0%-5%); glycolic acid (0%-5%); lactic acid (0%-5%); benzyl alcohol (0%-5%); ubiquinone (0%-0.5%); bisabolol (0%-1%); TEGO PEP 417® (0%-10%); Matrixyl® (glycerin, butylene glycol, carbomer, polysorbate 20, palmitoyl pentapeptide-4) (0%-10%); glutathione (0%-1%); superoxide dismutase (0%-5%); phenoxyethanol (0%-2%); sodium benzoate (0%-0.5%); and/or disodium EDTA (0%-0.2%). In other embodiments, the lower limit of any of the components above is about 0.00001%, about 0.0001%, about 0.001%, about 0.01% or about 0.1%.

In other embodiments of the present disclosure, the formulation may comprise (% w/w): 0.097539% purified water; 0.001% hydrolyzed sodium hyaluronate; 1% (aq) sodium hyaluronate; 0.000001% *Camellia sinensis* leaf extract; 0.000001% ascorbic acid; 0.000001% glycolic acid; 0.000001% lactic acid; 0.00025% benzyl alcohol; 0.000001% ubiquinone; 0.000001% bisabolol; 0.000001% Thiotaine®; 0.000001% TEGO PEP 417®; 0.000001% Matrixyl; 0.000001% glutathione; 0.000001% superoxide dismutase; 0.001% phenoxyethanol; 0.0001% sodium benzoate; and/or 0.0001% disodium EDTA.

In certain embodiments, the invention allows for much reduced dosing of potentially irritating and potentially tissue damaging ingredients. Observations in certain embodiments demonstrated significant benefits at dosages much reduced from those used topically. In certain embodiments, the invention achieved the results reported using physiological doses, those more commonly used in tissue culture experiments, such as fibroblast culture. Additionally, in certain embodiments, at the end of the subsequent procedure, e.g., microneedling procedure, a formulation of the present invention may be applied as a topical soothing and protective agent once the area of treatment is cleaned. In certain embodiments, the serum is soothing and provides a moisture reservoir to the treatment area, where the natural protective barrier of the skin has been damaged. In certain embodiments, this prevents one or more of dryness, discomfort, faster healing and improved treatment outcome.

DETAILED DESCRIPTION

In certain embodiments, the present disclosure provides a skincare formulation and methods of use thereof for alleviation or amelioration of dermatological conditions relating to dermatological procedures that irritate and/or wound human skin. Dermatological conditions amenable to treatments disclosed herein include, without limitation, inflammatory disorders of the skin and skin conditions characterized by increased cell turnover including psoriasis, photoaging, visible signs of extrinsic and intrinsic aging, yellowing, loss of elasticity, loss of collagen rich appearance and/or youthfulness, redness, dryness, age spots, skin wrinkles, acne, rosacea, ichthyosis, as well as skin cancers. In certain embodiments, the therapeutic formulations are also useful for improvement in one or more aesthetic criteria, including, but not limited to, a perceived improvement in apparent skin age, skin tone, weather-beaten appearance, yellowing, loss of elasticity, redness, dryness, age spots, skin wrinkles, skin smoothness, brightness, radiance, as well as skin pores becoming less noticeable. The therapeutic formulations are also useful for treating of melasma, i.e., hyper-pigmentation, including post-inflammatory hyper-pigmentation, patient discomfort, scarring, the stimulation of collagen growth, and providing effective healing to the skin of those undergoing treatments of the type noted herein.

As used herein, the terms "treatment" or "treating" with respect to a skin condition generally mean "having positive effect on a skin condition" and encompass reduction, amelioration, and/or alleviation of at least one symptom of a skin condition, a reduction, amelioration, and/or alleviation in the severity of the skin conditions, or delay, prevention, or inhibition of the progression of the skin condition. Treatment, as used herein, therefore does not require total curing of the condition. A formulation of the present disclosure that is useful for treatment of a skin condition, or a method of treating a skin condition, need only reduce the severity of a skin condition, reduce the severity of symptoms associated therewith, provide improvement to a patient's quality of life, or delay, prevent, or inhibit the onset of one or more symptoms of a skin condition. As used herein, these terms also encompass aesthetic improvements to the skin upon application of the disclosed formulations having a combination of, for example, an oligopeptide, antioxidants, one or more AHA, and hyaluronic acid or its derivatives.

As used herein, the terms "application," "apply," and "applying" with respect to a disclosed topical formulation or method of using a disclosed topical formulation, refer to any manner of administering a topical formulation to the skin of a patient which, in medical or cosmetology practice, delivers the formulation to the patient's skin surface. Smearing, rubbing, spreading, spraying a disclosed topical formulation, with or without the aid of suitable devices, on a patient's skin are all included within the scope of the term "application," as used herein. The term "topical" or "topically" with respect to administration or application of a disclosed skincare formulation refers to epicutaneous administration or application, onto skin.

As used herein, the phrase "effective amount" refers to an amount of a formulation of the present disclosure, or component thereof, effective to treat a skin condition as noted above, including a range of effects, from a detectable local improvement in an area of topical application to substantial relief of symptoms to an improvement in one or more aesthetic criteria, including, but not limited to, a perceived improvement in apparent skin dryness, keratosis pilaris, age, radiation damage, sun or UV damage, skin tone, weather-beaten appearance, yellowing, loss of elasticity, redness, dryness, age spots, skin wrinkles, skin smoothness, brightness, radiance, as well as skin pores becoming less noticeable. Effective amounts of the disclosed therapeutic formulations are also useful in certain embodiments for treating of melasma, i.e., hyper-pigmentation, including post-inflammatory hyper-pigmentation, patient discomfort, scarring, the stimulation of collagen growth, and providing effective healing to the skin of those undergoing treatments of the type noted herein. The effective amount will vary with the particular condition or conditions being treated, the severity of the condition, the duration of the treatment, the specific components of the composition being used, and other factors. More specifically, the disclosed compositions and formulations provide methods for therapeutic treatment of skin by providing, in some embodiments, a combination of hyaluronic acid, or its associated salts, and one or more of ascorbic acid, glycolic acid, lactic acid, in an efficacious manner to the skin. In certain embodiments, the disclosed compositions, formulations and methods of use thereof reduce, minimize, or eliminate normally-observed melasma, i.e., hyper-pigmentation, including post-inflammatory hyper-pigmentation, patient discomfort, scarring, stimulate collagen growth, and provide effective healing to the skin of those undergoing treatments of the type noted herein. Further benefits of certain embodiments include reducing, minimizing, or eliminating one or more of dry skin conditions including, inter alia, conditions characterized by keratosis pilaris, itching, severe skin flaking, breakdown of the skin barrier, discomfort, extreme dryness, cracking of the skin and sensitization. In certain embodiments, the disclosed compositions, formulations, and methods of use thereof also provide aesthetic improvements in the skin, including but not limited to skin that appears younger, skin exhibiting a more even tone, skin in which the pores are less noticeable, and skin that is judged by the user to be smoother, and/or to be improved with respect to its weather-beaten or aged appearance, yellowing, loss of elasticity, redness, dryness, age spots, and/or skin wrinkles.

As used herein, the phrase "skin barrier" refers to the outermost layer of the skin's surface. As is generally known, the skin barrier has cells and lipids, and may also be referred to as the permeability barrier, moisture barrier, or lipid barrier. The skin barrier prevents evaporation of essential water and electrolytes from the skin, among other functions. As disclosed herein, various processes of certain embodiments may disrupt, i.e., weaken or affect, the skin barrier causing, among others, pain, swelling, redness, dryness, irritation, which require healing and repair. The extent of skin barrier disruption may vary based on the specific dermatological procedure from minor penetration to depths that draw blood to the skin surface. For example, microneedling procedures may be adjusted for depths of penetration based on the skin conditions under treatment. Various dermatological procedures are used for promoting collagen production to treat skin conditions.

As used herein, the term "on an active basis" refers to the actual percentage or composition of an active ingredient, such as a peptide, as used in a formulation.

As used herein, the singular forms "a," "an," and "the" include plural references unless the context clearly indicates otherwise. Thus, for example, reference to a "formulation" includes a single formulation as well as multiple formulations and the like.

As used herein, the term "about" in connection with a measured quantity or time, refers to the normal variations in that measured quantity or time, as expected by one of ordinary skill in the art in making the measurement and exercising a level of care commensurate with the objective of measurement. In certain embodiments, the term "about" includes the recited number ±10%, such that "about 10" would include from 9 to 11, or "about 1 hour" would include from 54 minutes to 66 minutes.

In addition to the foregoing, the present disclosure in certain embodiments contemplates use of additional methods of applying the formulation including, but not limited to, spray aerosol, cotton pads and balls, gauze, foam, tissue applicators, human hands, among others.

In certain embodiments, the skincare formulation and delivery system disclosed herein not only maintain the active properties of the active agents, but also provide a greater efficiency of the active agents. In one embodiment of this disclosure, the skin is human skin. In other embodiments of the present disclosure, the skin is that of a companion animal, a domestic animal, or a commercially useful animal.

The present inventors have found that the treatments of the present disclosure are effective therapeutically for treating dermatological conditions. In certain embodiments of the present disclosure, a skincare formulation is provided having about 0.1% to about 5% or about 1% w/w of sodium hyaluronate, for example, a 1% w/w solution of honeycomb array sodium hyaluronate, from 0.05 ppm to 10 ppm or 3 ppm of one or more of ascorbic acid, glycolic acid, or lactic acid, from 1 ppm to 10 ppm or 7 ppm of an antioxidant, and from 0.00001% to about 1% or 0.001% w/w of hydrolyzed sodium hyaluronate.

In one embodiment, the skincare formulation of the present disclosure may have one or more organic acid, in particular, organic acids having molecular weight less than 300 g/mol, including, but not limited to, glycolic acid and alpha hydroxy acids (AHA), such as less than 12 carbons in length, including, but not limited to, salicylic or beta hydroxy acids, ascorbic acid, dicarboxylic acids, mandelic acid, pyruvic acid, tartaric acid, citric acid, malic acid, lactic acid, among others.

In certain embodiments, the disclosed compositions may also comprise one or more moisturizer and/or humectant.

Humectants are hygroscopic substances used to keep things moist, often a molecule with several hydrophilic groups, or capable of hydrogen bonding with water, or having other polar organic functional groups. Humectants can also function as solvents or cosolvents.

Some examples of humectants include, but are not limited to, amino acids; glycols and polyols, such as propylene glycol, hexylene glycol, and butylene glycol, including polymeric and sugar-based polyols/alcohols, for example, glycerol, sorbitol, xylitol, maltitol, polydextrose; mucopolysaccharides and carbohydrates, for example, aloe vera gel, yucca extract, dextrose and polydextrose; alpha hydroxy acids such as glycolic acid, lactic acid; albumen; esters or amides of acetic acid or similar; soluble carbohydrates, such as sugar, honey; salts, such as potassium chloride, sodium PCA, salts of polycarboxylic acids; amides, such as urea and urea derivatives.

In some embodiments, the skincare formulation may include a lubricant or a gliding agents, i.e., ingredients that provide "slip" of any kind, including, but not limited to, hyaluronic acid or its salts, solutions and derivatives thereof; cellulosic gums, solutions of and esters and salts or derivatives thereof, for example, carboxymethylcellulose, sodium carboxymethylcellulose, hydroxyethylcellulose, hydroxypropyl methylcellulose, cellulose gum, microcrystalline cellulose, C12-16 Alkyl PEG-2 Hydroxypropyl hydroxyethyl ethylcellulose; natural gums and biopolymers, solutions of and esters and salts or derivatives thereof, for example, gellan gum, xanthan gum, tragacanth gum, locust bean gum, guar gum, acacia gum, sclerotium gum, astragalus gum, biosaccharides, hydrated starch solutions, gelatin, mucilages, hydrocolloids, chitosan; polymers, synthetic and otherwise, for example, carbomers, acrylic acid resins, polyacrylamides, sodium polyacrylate, sodium C8-16 isoalkylsuccinyl lactoglobulin sulfonate, acrylates copolymer, acrylates/steareth-20 itaconate copolymer, PVM/MA decadiene crosspolymer, glyceryl acrylate/acrylic acid copolymer, Lubrajel™, among others.

In one embodiment, the moisturizer and/or humectant is sodium hyaluronate, such as fractionated and long-chain sodium hyaluronate, from single monomer to about 5 million Daltons, to bind moisture to the skin and penetrate the skin carrying moisture. Hyaluronate is a moisture binder that helps keep the skin hydrated and provides "slip" (sensory aesthetics) to the disclosed formulations.

The present formulations may also comprise one or more solubilizing agent, rheology modifier and/or emulsifier.

In some embodiments, the skincare formulation of the present disclosure may include one or more solubilizing agent/emulsifier, but such is not always required. More specifically, one or more solubilizing agent/emulsifier may be included when hydrophobic components in the formulation are in concentrations exceeding individually, or collectively, carrying capacity of the diluent, such as, water or water and humectants listed in the disclosure.

In one embodiment, the solubilizing agent/emulsifier is a non-ionic solubilizing agent/emulsifier. In another embodiment, the solubilizing agent/emulsifier is polysorbate 20.

In other embodiments, the emulsifier may be one or more of PEG-100 stearate. cetearyl alcohol, cetearyl glucoside, polysorbate 60, stearyl alcohol, glyceryl stearate, sodium polyacrylate, emulsifying wax.

In further embodiments of the formulation, xanthan gum, such as Keltrol T®, may be provided as an emulsifier for a stable emulsion.

In certain embodiments of the formulation, an artificial thickening agent, such as Rapithix A-60® from Ashland Chemical, may be provided.

The treatments and formulations may also comprise one or more soothing antioxidants to calm the skin and reduce inflammation.

Antioxidants inhibit oxidation, a type of chemical reaction that may produce free radicals. Antioxidants may assist in modulating inflammation, preventing or diminishing allergic or irritant reactions in the skin, including overstimulation of histamine up-regulation.

In this, in the formulations and treatments antioxidants assist in reducing the sting and irritation normally associated with application of high levels of active ingredients, as well as calming the existing condition for which the skin is being treated. This brings relief to the user, which leads to heightened compliance with the subject's treatment protocols.

Exemplary antioxidants include, but are not limited to, polyphenols, ergothioneine, glutathione, tetrahexyldecyl ascorbate, ascorbate derivatives, tocopherols or derivatives thereof, herbals such as pomegranate, cranberry, quercetin, carotenoids, resveratrol, ferulic acid, caffeic acid, gallic acid, topical compounds preventing or reducing the number of oxidative events in the skin, whether or not induced by UV light or solar exposure.

More specifically, various anti-irritant and anti-inflammatory agents contemplated by certain embodiments of the present disclosure include, but are not limited to, hydrocortisone, betamethasone, topical corticosteroids, diphenhydramine, licorice extract, arnica, turmeric, cucumber extract, green tea, zinc oxide, centella asiatica, mugwort, colloidal oatmeal, burdock, chamomile, camphor, resveratrol, hops, blue tansy, oatmeal, white willow bark, rose hips, tamanu oil, sandalwood, aloe vera, yucca extract, witch hazel, tea tree, menthol, cornflower extract, frankincense, balm mint, ginger extract, niacin, mallow, astaxanthin, sage extract, manuka honey, raspberry extract, alpha lipoic acid, glycerin, allantoin, urea, prostaglandin E3, ceramides, eicosapentaenoic acid, niacinamide, docosahexaenoic acid, hyaluronic acid, pycnogenol, mupirocin calcium USP, acetylsalicylic acid, clotrimazole, terbinafine hydrochloride.

In some embodiments, the antioxidant is a polyphenol. In a more specific aspect of these embodiments, the antioxidant comprises a polyphenol isolate of *Camellia sinensis*. The antioxidant can be a polyphenol, or a mixture thereof, that is isolated from plants, chemically synthesized; the antioxidant can also be a semi-synthetic compound prepared by modification of a natural polyphenol or mixture of polyphenols.

In specific embodiments of the present disclosure, the antioxidant includes "green tea polyphenols" isolated and purified from the leaves of *Camellia sinensis* plants. These antioxidants, as formulated and delivered herein, provide antioxidant activity as well as anti-inflammatory activity, and, further, provide skin soothing, protection, and repair activity.

Other antioxidants may include, but are not limited to, vitamin E acetate.

The treatments and formulations may also include one or more emollients. Emollients soften, lubricate and protect the skin from trans-epidermal water loss (TEWL). Some examples of emollients include, but are not limited to, lipids, phospholipids, occlusives, petrolatum, waxes, paraffinic oils, vegetable and animal fats, esters, such as isopropyl myristate, dicaprylyl carbonate, isopropyl palmitate, ethoxylates or propoxylates esters and fats, silicones, butters (cocoa butter, shea butter, etc.) and polyethylene glycols (PEG).

Skin lipids are the "mortar" in the brick and mortar model of the skin. These fats, oils and waxes may have more or less hydrophilic tendency and help prevent trans-epidermal water loss (TEWL), and allow the skin to retain moisture and more effectively repair itself. Examples are ceramides, phospholipids, phytosphingosine, cholesterol, lanosterol, fatty acids, sebum components, many of which can exist and be functional in their natural form, or be functional in the presently disclosed compositions and treatments as a derivative or synthetic analog.

In one embodiment, the emollient is an ester or oil. In other embodiments, the emollient may include, without limitation, one or more of the following shea butter, cocoa butter, mineral oil, lanolin, petrolatum, paraffin, beeswax, squalene, squalane, cetyl alcohol, olive oil, triethylhexanoin, coconut oil, jojoba oil, sesame oil, almond oil, or other plant oils, lipids, and combinations of two or more thereof.

Other emollients contemplated by the present disclosure include, but are not limited to, caprylic/capric triglyceride.

The formulation may also include other skin soothing agents, such as antioxidants, to reduce skin inflammation and irritation, and biomimetic ceramide complex that mimics the skin's natural lipid profile.

In certain embodiments of the presently disclosed formulation, ingredients therein include amino acid mixtures having one or more amino acids. In certain embodiments, the amino acid mixtures have a profile of the human skin's natural moisturizing factor (NMF).

In other embodiments of the present disclosure, the skin treatment formulation may include an amino acid or amino acid mixture, having a profile of the human skin's natural moisturizing factor (NMF), including one or more of the following components: water, e.g., purified water (QS to 100%), disodium EDTA, glycine, L-citrulline, L-alanine, L-proline, L-ornithine monohydrochloride, L-arginine, L-glutamic acid, L-histidine, valine, L-lysine, L-aspartic Acid, leucine, threonine, tyrosine, DL-phenylalanine, taurine, L-isoleucine, methionine, serine. Each individual amino acid may be present in a suitable amount (w/w), e.g., from about 0.001% to about 5%, from about 0.01% to about 2% or from about 0.1% to about 1%. In certain embodiments, the amount may be as follows for one or more amino acid: disodium EDTA (0.10%), glycine (1.612%), L-citrulline (1.00%), L-alanine (0.921%), L-proline (0.148%), L-ornithine monohydrochloride (0.287%), L-arginine (0.073%), L-glutamic acid (0.243%), L-histidine (0.429%), valine (0.381%), L-lysine (0.179%), L-aspartic Acid (0.30%), leucine (0.262%), threonine (0.713%), tyrosine (0.295%), DL-phenylalanine (0.283%), taurine (0.032%), L-isoleucine (0.194%), methionine (0.072%), serine (2.32%). In certain embodiments of the present disclosure, the formulations may include one or more solubilizing/emulsifying, skin-conditioning/treating agent and preservatives/stabilizing agent, such as butylene glycol, caprylic/capric triglyceride, phospholipids, SK-Influx V®, glycerin, lecithin, tocopheryl acetate, ubiquinone (co-enzyme Q10), hydrolyzed glycosaminoglycans, hexanoyl dipeptide-3 norleucine acetate, *Salix nigra* (willow) bark extract, mandelic acid, bisabolol, ceramide NP, ceramide AP, phytosphingosine, cholesterol, ceramides EOP, glycine, citrulline, alanine, proline, ornithine HCl, arginine, glutamic acid, histidine, valine, lysine, aspartic acid, leucine, threonine, tyrosine, phenylalanine, taurine, isoleucine, methionine, serine, sodium lauroyl lactylate, hydrogenated polydecene, trideceth-6, xanthan gum, carbomer, sodium benzoate, phenoxyethanol, disodium EDTA.

In one embodiment of the present disclosure, the skin treatment formulation may include two or more of the following ingredients: purified water, hydrolyzed sodium hyaluronate, sodium hyaluronate, ascorbic acid, glycolic acid, lactic acid, *Camellia sinensis* leaf extract, benzyl alcohol, ubiquinone, bisabolol, Thiotaine®, TEGO PEP 417®, Matrixyl (glycerin, butylene glycol, carbomer, polysorbate 20, palmitoyl pentapeptide-4), glutathione, superoxide dismutase, phenoxyethanol, sodium benzoate, disodium EDTA.

In certain embodiments of the present disclosure, the formulations may be sterile formulations.

In other embodiments of the present disclosure, the skin treatment formulation may include two or more of the following components: water, e.g., purified water, hydrolyzed sodium hyaluronate, sodium hyaluronate, *Camellia sinensis* leaf extract, ascorbic acid, glycolic acid, lactic acid, benzyl alcohol, ubiquinone, bisabolol, collagen boosting tetrapeptide (TEGO PEP 417®), Matrixyl® (glycerin, butylene glycol, carbomer, polysorbate 20, palmitoyl pentapeptide-4), glutathione, superoxide dismutase phenoxyethanol, sodium benzoate, or disodium EDTA.

In other embodiments of the present disclosure, the skin treatment formulation may include two or more of the following components formulated within the indicated ranges (all expressed as % (w/w)): purified water (10%-99.8%), hydrolyzed sodium hyaluronate (0.1%-25%), sodium hyaluronate (0.1%-10%), *Camellia sinensis* leaf extract (0.001%-1%), ascorbic acid (0.1%-5%), glycolic acid (0.1%-5%), lactic acid (0.1%-5%), benzyl alcohol (0.1%-5%), ubiquinone (0.1%-0.5%), bisabolol (0.01%-1%), collagen boosting tetrapeptide, TEGO PEP 417 ® (0.1%-10%), Matrixyl® (glycerin, butylene glycol, carbomer, polysorbate 20, palmitoyl pentapeptide-4) (0.1%-10%), glutathione (0.1%-1%), superoxide dismutase (0.1%-5%), phenoxyethanol (0.1%-2%), sodium benzoate (0.1%-0.5%), or disodium EDTA (0.1%-0.2%). In certain embodiments, the lower limit of any of the components above is 1%, 0.1%, 0.001%, 0.0001%, 0.00001%, 0.000001% or 0.0000001%.

In other embodiments of the present disclosure, the skin treatment formulation may include two or more of the following components formulated within the indicated ranges (all expressed as % (w/w)): purified water (50%-99.8%), hydrolyzed sodium hyaluronate (0%-25%), sodium hyaluronate (0.1%-10%), *Camellia sinensis* leaf extract (0%-1%), ascorbic acid (0%-5%), glycolic acid (0%-5%), lactic acid (0%-5%), benzyl alcohol (0%-5%), ubiquinone (0%-0.5%), bisabolol (0%-1%), collagen boosting tetrapeptide, TEGO PEP 417® (0%-10%), Matrixyl® (glycerin, butylene glycol, carbomer, polysorbate 20, palmitoyl pentapeptide-4) (0%-10%), glutathione (0%-1%), superoxide dismutase (0%-5%), phenoxyethanol (0%-2%), sodium benzoate (0%-0.5%), or disodium EDTA (0%-0.2%).

In certain embodiments of the present disclosure, the formulation may include two or more of the following ingredients formulated within the indicated ranges (all expressed as % (w/w)): purified water (0.097539%), hydrolyzed sodium hyaluronate (0.001%), sodium hyaluronate (1% (aq)), *Camellia sinensis* leaf extract (0.000001%), ascorbic acid (0.000001%), glycolic acid (0.000001%), lactic acid (0.000001%), benzyl alcohol (0.00025%), ubiquinone (0.000001%), bisabolol (0.000001%), Thiotaine® (0.000001%), TEGO PEP 417® (0.000001%), Matrixyl® (glycerin, butylene glycol, carbomer, polysorbate 20, palmitoyl pentapeptide-4) (0.000001%), glutathione (0.000001%), superoxide dismutase (0.000001%), phenoxyethanol (0.001%), sodium benzoate (0.0001%), and disodium EDTA (0.0001%).

All reference to purified water herein can also be substituted generally with water.

Topical application of the formulations may include application to specific body areas, such as, without limitation, feet, elbows, knees, that are susceptible to dermatological conditions of the type requiring the therapeutic treatments disclosed herein. Such treatments may be applied, for example, 1-3 times per day, for example, before and/after dermatological procedures of affected areas, followed by regular topical applications, as desirable or necessary, to maintain the improved condition of the body areas under treatment. In certain embodiments, the actual dosage of the formulations of the present disclosure to be topically applied to the skin will depend on, inter alia, the condition to be treated, the particular regimen to be followed, and the personal preferences of the user.

Formulations of the present disclosure may be prepared under ambient conditions. In certain embodiments, formulations of the present disclosure are prepared under an inert atmosphere. In particular, the inert atmosphere is an inert gas, such as but not limited to, nitrogen, argon, or combinations thereof. In certain embodiments, formulations of the present disclosure are prepared under a dry inert atmosphere, which may comprise, consist essentially of, or consist of one or more dry inert gas, including but not limited to dry nitrogen, dry argon, or a combination thereof.

Exemplary Composition Ranges

The formulation of the present disclosure may have the following composition presented in Tables 1 and 2.

TABLE 1

Example 1

| Ingredient | % (w/w) |
| --- | --- |
| Sodium hyaluronate | 0.1-10 |
| Water | 50-99.8 |
| Hydrolyzed sodium hyaluronate | 0-25 |
| Ascorbic acid | 0-5 |
| Glycolic acid | 0-5 |
| Lactic Acid | 0-5 |
| Green tea polyphenols | 0-1 |
| Benzyl alcohol | 0-5 |
| Ubiquinone | 0-0.5 |
| Bisabolol | 0-1 |
| Ergothioneine | 0-1 |
| Tego Pep 4-17 ® or equivalent | 0-10 |
| Matrixyl ® or equivalent | 0-10 |
| Glutathione | 0-1 |
| Superoxide dismutase sol. (Lonza Biocell SOD) | 0-5 |
| Disodium EDTA | 0-0.2 |
| Phenoxyethanol | 0-2 |
| Sodium Benzoate | 0-0.5 |

TABLE 2

Example 2

| Ingredient | % (w/w) |
| --- | --- |
| Sodium hyaluronate | 1 |
| Purified Water | 0.097539% |
| Hydrolyzed sodium hyaluronate | 0.001% |
| Ascorbic acid | 0.000001% |
| Glycolic acid 99% | 0.000001% |
| Lactic Acid 90% | 0.000001% |
| Camellia Sinensis Leaf Extract 90% | 0.000001% |
| Benzyl alcohol | 0.00025% |
| Ubiquinone | 0.000001% |
| Bisabolol | 0.000001% |
| Thiotaine | 0.000001% |
| Tego Pep 4-17 ® (Glycerin, Butylene Glycol, Water, Tetrapeptide-21) | 0.000001% |
| Matrixyl ® (Glycerin, Butylene Glycol, Carbomer, Polysorbate 20, Palmitoyl Pentapeptide-4) | 0.000001% |
| Glutathione | 0.000001% |
| Superoxide dismutase | 0.000001% |
| Disodium EDTA | 0.0001% |
| Phenoxyethanol | 0.01% |
| Sodium Benzoate | 0.0001% |

TABLE 3

Example 3

| Ingredient | % (w/w) |
| --- | --- |
| Sodium hyaluronate (1% solution) | 99.73% |
| Sodium Hyaluronate Hydrolyzed | 0.010% |
| L Ascorbic acid | 0.0001% |
| Glycolic acid 99% | 0.000001% |
| Lactic Acid 90% | 0.0001% |
| Green Tea Polyphenols 90% | 0.000001% |
| Benzyl alcohol | 0.00250% |
| Co Q10 Powder | 0.000001% |
| Bisabolol | 0.000001% |
| Ergothioneine | 0.000001% |
| Tego Pep 4-17 ® | 0.000001% |
| Matrixyl ® | 0.000001% |
| Bioalkemia Batch Glutathione 201608001M | 0.000001% |
| Superoxide dismutase | 0.000001% |
| Disodium EDTA | 0.05% |
| Phenoxyethanol | 0.20% |
| Sodium Benzoate | 0.01% |
| Total | 100% |

List of Certain Embodiments

In a first embodiment, a method for therapeutic treatment of skin in dermatological procedures affecting the skin's barrier, comprising: applying to skin selected for a dermatological procedure affecting the skin's barrier a therapeutically effective amount of a formulation comprising hyaluronic acid, or its associated salts, and one or more of ascorbic acid, glycolic acid, lactic acid, wherein the hyaluronic acid or its associated salts is at least 1% (w/w) and each of the ascorbic acid, glycolic acid, lactic acid is at least 1 ppm; and performing the dermatological procedure on the skin.

The method of the first embodiment, wherein the dermatological procedures include microneedling, laser, chemical peels, intense light therapy, microdermabrasion, dermaplaning.

The method of the first embodiment, wherein performing the dermatological procedure comprises applying a microneedling procedure to the skin.

The method of the first embodiment, further comprising applying the formulation before the microneedling procedure.

The method of the first embodiment, further comprising applying the formulation after the microneedling procedure.

The method of the first embodiment, wherein the salt of hyaluronic acid is sodium hyaluronate.

The method of the first embodiment, wherein the sodium hyaluronate is a solution of honeycomb array sodium hyaluronate.

The method of the first embodiment, wherein the formulation further comprises an antioxidant, wherein the antioxidant is one or more of Camellia sinensis leaf extract, Camellia sinensis polyphenols, ascorbic acid, ubiquinone, bisabolol, Thiotaine®, ergothioneine, glutathione, superoxide dismutase.

The method of the first embodiment, wherein the formulation further comprises one or more of purified water, hydrolyzed sodium hyaluronate, sodium hyaluronate, Camellia sinensis leaf extract, benzyl alcohol, ubiquinone, bisabolol, Thiotaine®, TEGO PEP 417 ®, Matrixyl® (glycerin, butylene glycol, carbomer, polysorbate 20, palmitoyl pentapeptide-4), glutathione, superoxide dismutase, phenoxyethanol, sodium benzoate, disodium EDTA.

The method of the first embodiment, wherein the formulation is a sterile formulation.

In a second embodiment, a formulation for therapeutic treatment of skin in dermatological procedures affecting the skin's barrier, comprising hyaluronic acid, or its associated salts, and one or more of ascorbic acid, glycolic acid, lactic acid, wherein the hyaluronic acid or its associated salts is at least 1% (w/w) and each of the ascorbic acid, glycolic acid, lactic acid is at least 1 ppm.

The formulation of the second embodiment, comprising (% w/w):
  purified water (50%-99.8%);
  hydrolyzed sodium hyaluronate (0%-25%);
  sodium hyaluronate (0.1%-10%);
  *Camellia sinensis* leaf extract (0%-1%);
  ascorbic acid (0%-5%);
  glycolic acid (0%-5%);
  lactic acid (0%-5%);
  benzyl alcohol (0%-5%);
  ubiquinone (0%-0.5%);
  bisabolol (0%-1%);
  TEGO PEP 417® (0%-10%);
  Matrixyl® (glycerin, butylene glycol, carbomer, polysorbate 20, palmitoyl pentapeptide-4) (0%-10%);
  glutathione (0%-1%);
  superoxide dismutase (0%-5%);
  phenoxyethanol (0%-2%);
  sodium benzoate (0%-0.5%);
  disodium EDTA (0%-0.2%).

The formulation of the second embodiment, comprising (% w/w):
  0.097539% purified water;
  0.001% hydrolyzed sodium hyaluronate;
  1% (aq) sodium hyaluronate;
  0.000001% *Camellia sinensis* leaf extract;
  0.000001% ascorbic acid;
  0.000001% glycolic acid;
  0.000001% lactic acid;
  0.00025% benzyl alcohol;
  0.000001% ubiquinone;
  0.000001% bisabolol;
  0.000001% Thiotaine®;
  0.000001% TEGO PEP 417®;
  0.000001% Matrixyl;
  0.000001% glutathione;
  0.000001% superoxide dismutase;
  0.001% phenoxyethanol;
  0.0001% sodium benzoate;
  0.0001% disodium EDTA.

The formulation of the second embodiment, wherein the salt of hyaluronic acid is sodium hyaluronate.

The formulation of the second embodiment, wherein the sodium hyaluronate is a solution of honeycomb array sodium hyaluronate.

The formulation of the second embodiment, further comprising an antioxidant, wherein the antioxidant is one or more of *Camellia sinensis* leaf extract, *Camellia sinensis* polyphenols, ascorbic acid, ubiquinone, bisabolol, Thiotaine®, ergothioneine, glutathione, superoxide dismutase.

The formulation of the second embodiment, further comprising one or more of purified water, hydrolyzed sodium hyaluronate, sodium hyaluronate, *Camellia sinensis* leaf extract, benzyl alcohol, ubiquinone, bisabolol, Thiotaine®, TEGO PEP 417®, Matrixyl® (glycerin, butylene glycol, carbomer, polysorbate 20, palmitoyl pentapeptide-4), glutathione, superoxide dismutase, phenoxyethanol, sodium benzoate, disodium EDTA.

The formulation of any preceding embodiment, wherein the formulation is a sterile formulation.

Illustrative Examples

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Efficacy and Safety of Microneedling Combined with Sterile Hyaluronic Acid Serum for Acne Scars, Rhytides and Skin Texture A study was conducted to measure the efficacy and safety of microneedling with sterile hyaluronic acid on improving skin texture and reducing the appearance of acne scars and rhytides. The aim of the study is to test the safety and efficacy of sterile hyaluronic acid during and after microneedling treatments. Because hyaluronic acid is inherent to our skin and by utilizing a sterile form of it, it is unlikely that subjects have a hypersensitivity response. Furthermore, hyaluronic acid can further enhance the subject's improvement in acne scarring and skin texture by stimulating fibroblasts which cause collagen synthesis.

The following products were used in this study: Topix Sterile Hyaluronic Acid Serum; Topix Replenix green tea fortified Cleanser #836; Topix #1030 sterile post procedure mask; Topix #895 Replenix Restorative Nighttime moisturizer; and Topix #858 Replenix Sheer Physical Sunscreen SPF 50.

To be considered as a subject, each candidate must:
  Be between the ages of 18-70;
  have acne induced pits and scars and fine lines on the face
  be in good general health;
  willing to avoid sun exposure (as best as possible) to the face including sunbathing; using tanning booths, and self-tanning products for the duration of the study.
  express willingness to cooperate with the investigator and comply to study requirements;
  demonstrate the ability to understand the purpose of the study and what is required of her to bring it to a meaningful conclusion;
  demonstrate the ability to understand what risks associated with participation are;
  demonstrate the ability to read and understand all the items in the informed consent document;
  sign the informed consent document of their free will and without any reservations A participant will be excluded if the interview and examination discloses any of the following:
  active moderate to severe acne on the face
  has a history of bleeding disorder, and/or is taking anticoagulants
  has a history of keloidal tendency
  a systemic illness or infection that contra-indicates participation;
  any dermatological disorders in the test areas; including atopic dermatitis, psoriasis, vitiligo, excessive freckles and discolorations etc.
  have any form of suspicious lesion or skin cancer on the treatment area;
  under a dermatologist's care for any conditions in the test areas;
  any infections, burns, cuts, tattoos, visible scars or acne in the test areas;
  pregnancy, lactation, or attempting to get pregnant as reported by the subject for three months prior or for the duration of the study;

use of acne medication including isotretinoin and other retinoids (excluding OTC benzoyl peroxide products) within the previous 3 months participated in a study involving the face in the last 1 month prior to baseline visit;

receipt of any skin treatments in the last 6 months (i.e. skin peels, skin resurfacing);

Market Research Companies, and Cosmetic/Personal Care Manufacturers are excluded from participation in clinical studies Microneedling Procedure Administered by the Dermatologist The subjects arrived for the baseline visit with clean skin free of any creams, perfume powders and treatment products. Inclusion/Exclusion Criteria was verified. Subjects who met all the study requirements were enrolled.

Photographs were obtained using two 3D cameras: 3D LifeViz Micro Camera and 3D LifeViz Mini Camera as per standard operating procedure submitted by QuantifiCare. Four photographs were obtained using the 3D LifeViz Mini Camera and three closeup photos of the scars will be obtained using 3D LifeViz Micro Camera.

The subjects received a microneedling treatment with the sterile HA serum as described below. The subjects received a post care kit with detailed instructions to take home. A total of 10 subjects participated in the study.

One month after first treatment: Photographs were obtained as described below. The subjects answered a questionnaire to determine their perception of product and treatment effect. The subjects received a second treatment of hyaluronic acid serum and microneedling as described below. The subjects received test materials and instructions to take home.

One month after second treatment: Photographs were obtained. The subjects answered a questionnaire to determine their perception of product and treatment effect. The subjects received a third treatment of hyaluronic acid serum and microneedling. The subjects received test materials and instructions to take home.

One month after third treatment: Photographs were obtained. The subjects answered a questionnaire to determine their perception of product and treatment effect. The subjects returned all unused products and empty containers.

HA and Microneedling treatment: The subjects received a microneedling treatment with sterile hyaluronic acid serum and microneedling. The entire face was anesthetized with a topical cream containing Benzocaine 20%, Lidocaine 6% and Tetracaine 4% (BLT) for 10-15 minutes prior to treatment. The cream was removed from the face using chlorohexidine followed by alcohol. The sterile hyaluronic acid serum (HA serum) was applied all over the face using a sterile syringe. Then the face was microneedled in a vertical, horizontal and circular pattern at a depth of 1.0 on the forehead and 2.0 on the entire face. Upon completion, the face was wiped of excess blood and #1030 sterile post procedure mask was applied for 10 minutes after which the skin of the subjects was wiped, and another layer of the sterile HA serum was applied and allowed to absorb for 5 minutes. The subjects then applied a sunscreen (#858 SPF 50 sunscreen).

Care Instructions: Post-operative care included use of regimen of products provided described below. The subjects were instructed to avoid touching or picking their face for the course of the study.

Post-Care Treatment Instructions:
Morning:
Wash with Cleanser #836

Apply moisturizer #885 after washing followed by sunscreen #858

Evening:

Wash with cleanser #836

For the first 4 days use the sterile post procedure mask #1030 for 15 minutes as instructed in the video shown to the subjects at the first visit.

then apply moisturizer #895

Photography: Three dimensional Photographs of the full face of the subjects were obtained using 3D LifeViz™ mini (QuantifiCare, San Francisco CA) is stereovision camera equipped with dual LED pointer technology. This technology also produces high quality 3D reconstructions that allows visualization and quantification of the target areas in 3D with a depth precision of 25 microns. This method is useful for measurements of surface, depth, height, volume etc. Four pictures were obtained from this camera, at each visit: Front view, Right, left and front low-angled chin view 3D LifeViz Micro Camera (QuantifiCare, San Francisco CA) is a stereovision camera equipped with dual LED pointer technology that produces high quality 3D reconstructions which allows visualization and accurately quantification of target areas in 3D with a depth precision of 8 microns and a Field of View of 5×7 cm. This method is useful for measurements of surface, depth, height, volume etc. Three photographs were obtained from this camera at each visit: forehead, right and left cheek.

Results and Statistical Analysis

The images were analyzed by personnel at Bergen Dermatology. All data was evaluated by Neelam Muizzuddin, PhD at SCR Consultants. From this analysis, it was found that the usual issues and complications which have been reported in the literature were not observed. Without being limited to a theory, it is believed that this was primarily due to the raw material selection and dosing, as well as a much higher than expected synergy of the ingredient effects. The vehicle, hyaluronic acid is a glycosaminoglycan polysaccharide and a physiological component of the extracellular matrix. Hyaluronic acid may further enhance the subject's improvement in acne scarring and skin texture by stimulating fibroblasts which cause collagen synthesis. This biocompatibility and dosing reduced the observed irritation much below expectations and provides for a product which is free of the risk of granuloma. There were no withdrawals or treatment needed due to adverse reactions. Post procedure care was well tolerated primarily due to the lower irritation and inflammation experienced as a result of the procedure.

Clinical grading with respect to treatment of acne scarring, wrinkles (especially fine lines) and improved skin texture showed statistically significant results. With respect to acne scarring, subjects showed about a 20% reduction in scarring.

An improved treatment outcome was achieved over conventional microneedling with clinical assessments showing much better than expected avoidance of pain, irritation, redness, onset of papules, pustules or milia, swelling and dryness and discomfort. In addition to improved remediation of scarring, pitted areas, fine lines and wrinkles, overall tone and texture, firmness and plumping of the skin, which produces a collagen-rich appearance, was improved. This was presumed to improve because of the additional volume added by newly deposited collagen.

Figure 1:
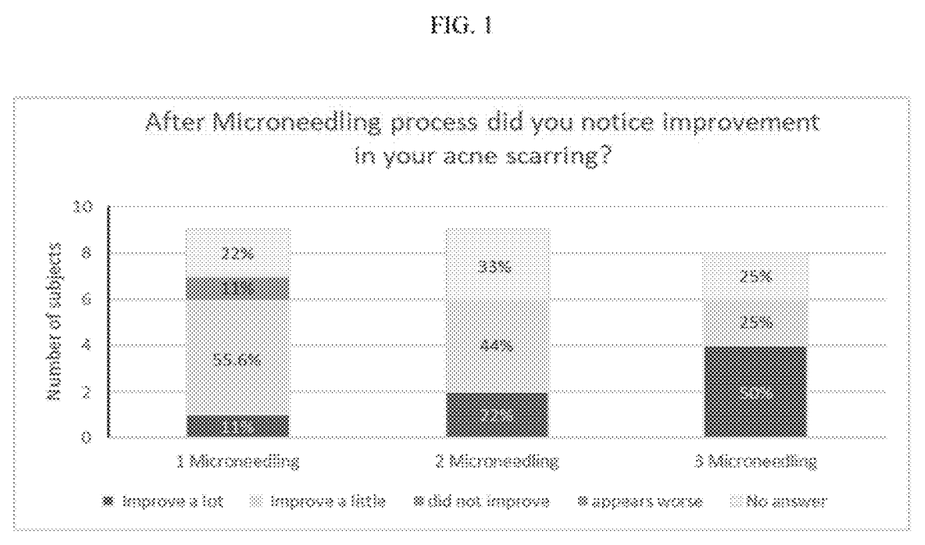
FIG. 1 is a bar graph illustrating the results of the questionnaire in the study relating to improvement in acne scarring.
Figure 2:
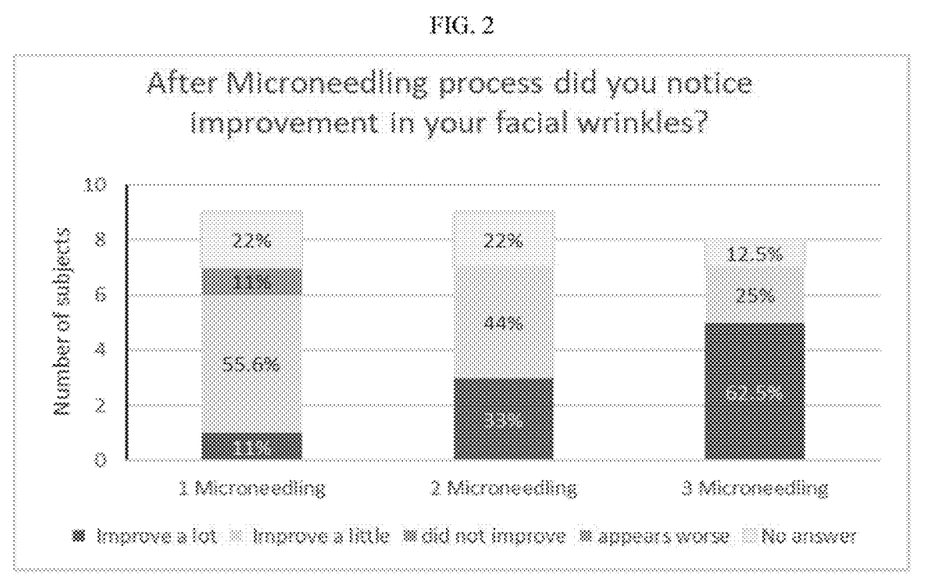
FIG. 2 is a bar graph illustrating the results of the questionnaire in the study relating to improvement in face wrinkles.
Figure 3:
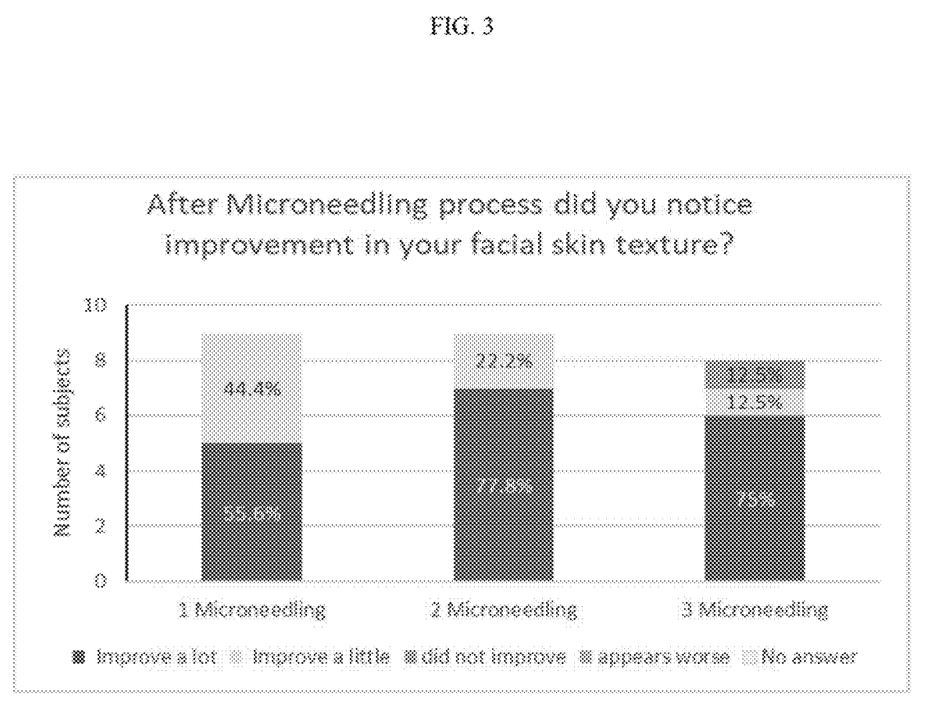
FIG. 3 is a bar graph illustrating the results of the questionnaire in the study relating to improvement in face skin texture.

FIGS. 1 to 3 represent the results of the questionnaire showing that the subjects found that the formulation and treatment improved acne scarring, face wrinkles and face skin texture.

What is claimed is:

1. A dermatological formulation, comprising sodium hyaluronate, an emulsifier, and glycolic acid, wherein the sodium hyaluronate is at least about 1% (w/w) and glycolic acid is at least about 1 ppm, and wherein the sodium hyaluronate is selected from a solution of honeycomb array sodium hyaluronate.

2. The dermatological formulation of claim 1, wherein the formulation comprises (% w/w):
   water in an amount of 50%-99.8%;
   hydrolyzed sodium hyaluronate in an amount of 0%-25%;
   sodium hyaluronate in an amount of 1%-10%;
   *Camellia sinensis* leaf extract in an amount of 0%-1%;
   ascorbic acid in an amount of 0%-5%;
   glycolic acid in an amount of 0%-5%;
   lactic acid in an amount of 0%-5%;
   benzyl alcohol in an amount of 0%-5%;
   ubiquinone in an amount of 0%-0.5%;
   bisabolol in an amount of 0%-1%;
   a combination of Glycerin, Butylene Glycol, Water, and Tetrapeptide-21 in an amount of 0%-10%;
   a combination of glycerin, butylene glycol, carbomer, polysorbate 20, and palmitoyl pentapeptide-4 in an amount of 0%-10%;
   glutathione in an amount of 0%-1%;
   superoxide dismutase in an amount of 0%-5%;
   phenoxyethanol in an amount of 0%-2%;
   sodium benzoate in an amount of 0%-0.5%; and
   disodium EDTA in an amount of 0%-0.2%.

3. The dermatological formulation of claim 1, wherein the formulation further comprises at least one of ascorbic acid and lactic acid.

4. The dermatological formulation of claim 1, further comprising an antioxidant.

5. The dermatological formulation of claim 4, wherein the antioxidant is one or more of *Camellia sinensis* leaf extract, *Camellia sinensis* polyphenols, ubiquinone, bisabolol, ergothioneine, glutathione, or superoxide dismutase.

6. The dermatological formulation of claim 1, further comprising one or more of purified water; hydrolyzed sodium hyaluronate; *Camellia sinensis* leaf extract; benzyl alcohol; ubiquinone; bisabolol; ergothioneine; a combination of glycerin, butylene glycol, water, and Tetrapeptide-21; a combination of glycerin, butylene glycol, carbomer, polysorbate 20, and palmitoyl pentapeptide-4; glutathione; superoxide dismutase; phenoxyethanol; sodium benzoate; or disodium EDTA.

7. The dermatological formulation of claim 6, wherein the formulation is a sterile formulation.

8. A method, comprising:
   applying a therapeutically effective amount of a dermatological formulation according to claim 1 to the skin; and
   performing a dermatological procedure on the skin.

9. The method of claim 8, wherein the dermatological procedure comprises microneedling, laser, chemical peels, intense light therapy, microdermabrasion, or derma-planing.

10. The method of claim 8, wherein the performing the dermatological procedure comprises applying a microneedling procedure to the skin.

11. The method of claim 10, further comprising applying the dermatological formulation before the microneedling procedure.

12. The method of claim 10, further comprising applying the dermatological formulation after the microneedling procedure.

13. The method of claim 8, wherein the dermatological formulation further comprises an antioxidant.

14. The method of claim 13, wherein the antioxidant is one or more of *Camellia sinensis* leaf extract, *Camellia sinensis* polyphenols, ascorbic acid, ubiquinone, bisabolol, ergothioneine, glutathione, superoxide dismutase.

15. The method of claim 8, wherein the formulation further comprises one or more of water, hydrolyzed sodium hyaluronate; *Camellia sinensis* leaf extract; benzyl alcohol; ubiquinone; bisabolol; ergothioneine; a combination of glycerin, butylene glycol, water, and Tetrapeptide-21; a combination of glycerin, butylene glycol, carbomer, polysorbate 20, and palmitoyl pentapeptide-4; glutathione; superoxide dismutase; phenoxyethanol; sodium benzoate; or disodium EDTA.

16. The method of claim 15, wherein the dermatological formulation is a sterile formulation.

\* \* \* \* \*